(12) United States Patent
Tsuboi et al.

(10) Patent No.: US 12,203,835 B2
(45) Date of Patent: Jan. 21, 2025

(54) FINE RATIO MEASURING METHOD AND APPARATUS

(71) Applicant: JFE STEEL CORPORATION, Tokyo (JP)

(72) Inventors: Toshiki Tsuboi, Tokyo (JP); Naoshi Yamahira, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 556 days.

(21) Appl. No.: 17/601,617

(22) PCT Filed: Apr. 3, 2020

(86) PCT No.: PCT/JP2020/015327
§ 371 (c)(1),
(2) Date: Oct. 5, 2021

(87) PCT Pub. No.: WO2020/204165
PCT Pub. Date: Oct. 8, 2020

(65) Prior Publication Data
US 2022/0205893 A1 Jun. 30, 2022

(30) Foreign Application Priority Data
Apr. 5, 2019 (JP) .................................. 2019-073085

(51) Int. Cl.
*G01N 15/0205* (2024.01)
*C21B 5/00* (2006.01)
*C21B 7/24* (2006.01)
*F27B 1/28* (2006.01)
*G01N 15/02* (2024.01)
*G01N 15/075* (2024.01)
(Continued)

(52) U.S. Cl.
CPC ............ *G01N 15/0205* (2013.01); *C21B 5/00* (2013.01); *C21B 5/006* (2013.01); *C21B 5/007* (2013.01);
(Continued)

(58) Field of Classification Search
CPC .. G01N 15/0205; G01N 15/075; G01N 15/02; G01N 33/00; G01N 2021/1765;
(Continued)

(56) References Cited

U.S. PATENT DOCUMENTS 6,577,756 B1    6/2003  Furui
2003/0185429 A1 10/2003  Furui
(Continued)

FOREIGN PATENT DOCUMENTS

CN    106459768 A    2/2017
EP      3147341 A1   3/2017
(Continued)

OTHER PUBLICATIONS

Xu et al. (A Real-Time 3D Measurement System for the Blast Furnace Burden Surface Using High-Temperature Industrial Endoscope. Sensors (Basel). Feb. 6, 2020;20(3):869. doi: 10.3390/s20030869. PMID: 32041296; PMCID: PMC7039294.) (Year: 2020).*
(Continued)

*Primary Examiner* — Manish S Shah
*Assistant Examiner* — Christian T Bryant
(74) *Attorney, Agent, or Firm* — Oliff PLC (57) ABSTRACT

A fine ratio measuring method and apparatus. The fine ratio measuring method includes a step S1 of measuring a distance between a distance measuring device and lumps of material, a step S2 of calculating a feature quantity from distance data obtained in the step S1, and a step S3 of converting the feature quantity calculated in step S2 to a fine ratio. The feature quantity calculated in step S2 represents distance variation calculated from the distance data obtained in the step S1. A higher fine ratio in lumps of material means greater microscopic distance variation caused by microscopic irregularities in the surface of the lumps of material in the height direction within a three-dimensional shape.
(Continued)

Therefore, by using the distance variation as the feature quantity, the fine ratio in the lumps of material can be measured in real time with high accuracy.

4 Claims, 5 Drawing Sheets

(51) Int. Cl.
*G01N 33/00* (2006.01)
*G01N 33/24* (2006.01)
*F27D 19/00* (2006.01)
*F27D 21/02* (2006.01)
*G01N 15/00* (2024.01)
*G01N 21/17* (2006.01)

(52) U.S. Cl.
CPC ............ *C21B 7/24* (2013.01); *C21B 2300/04* (2013.01); *F27B 1/28* (2013.01); *F27D 2019/0003* (2013.01); *F27D 2021/026* (2013.01); *G01N 2015/0061* (2013.01); *G01N 15/02* (2013.01); *G01N 15/075* (2024.01); *G01N 2021/1765* (2013.01); *G01N 33/00* (2013.01); *G01N 33/24* (2013.01)

(58) Field of Classification Search
CPC ....... C21B 5/00; C21B 2300/04; C21B 5/006; C21B 5/007; C21B 5/008; C21B 7/24; F27D 2019/0003; F27D 2021/026; F27D 1/28; F27B 1/28
See application file for complete search history.

(56) References Cited

U.S. PATENT DOCUMENTS

| | | |
|---|---|---|
| 2004/0131245 A1 | 7/2004 | Furui |
| 2005/0126342 A1 | 6/2005 | Sterneland et al. |

FOREIGN PATENT DOCUMENTS

| | | |
|---|---|---|
| JP | S58-217613 A | 12/1983 |
| JP | H05-164677 A | 6/1993 |
| JP | H06-127663 A | 5/1994 |
| JP | 2000-304648 A | 11/2000 |
| JP | 2000-329683 A | 11/2000 |
| JP | 2004-340822 A | 12/2004 |
| JP | 2005-134301 A | 5/2005 |
| JP | 2014-092494 A | 5/2014 |
| JP | 2015-124436 A | 7/2015 |
| JP | 2015-196888 A | 11/2015 |
| JP | 6207421 B2 | 10/2017 |
| RU | 2 299 242 C2 | 5/2007 |
| RU | 2 353 660 C2 | 4/2009 |
| WO | 2005/071119 A1 | 8/2005 |
| WO | 2011/023853 A2 | 3/2011 |
| WO | 2018/101287 A1 | 6/2018 |
| WO | 2018/181942 A1 | 10/2018 |

OTHER PUBLICATIONS

Jun. 30, 2020 International Search Report issued in International Application No. PCT/JP2020/015327.
Jan. 6, 2021 Office Action issued in Taiwanese Patent Application No. 109111462.
Feb. 9, 2021 Office Action issued in Japanese Patent Application No. 2020-544967.
Mar. 3, 2022 Extended European Search Report issued in European Patent Application No. 20784334.3.
Mar. 15, 2022 Office Action issued in Russian Patent Application No. 2021129024.
May 7, 2022 Office Action issued in Chinese Patent Application No. 202080026229.6.
Mar. 11, 2023 Office Action issued in Korean Patent Application No. 10-2021-7031388.

* cited by examiner

FINE RATIO MEASURING METHOD AND APPARATUS

TECHNICAL FIELD

This application relates to a fine ratio measuring technique for measuring the fine ratio, or the ratio of fines adhering to the surface of lumps of material, such as ore and coke, which are raw materials for blast furnaces.

BACKGROUND

In production processes that use raw materials, such as minerals, the distributions of the particle sizes of the raw materials affect the operation of the production processes. Therefore, it is necessary to measure the distributions of the particle sizes of the raw materials in advance. Particularly in the operation of a blast furnace, it is important to know the distributions of the particle sizes of raw materials, such as ore and coke, to ensure gas permeation in the furnace. It is also necessary to operate the blast furnace with attention to the ratios of fines (e.g., fines with a particle size of 5 mm or less) adhering to larger particles (lumps) of the raw materials.

To know the distributions of the particle sizes of raw materials in the conventional operation of a blast furnace, the particle sizes have been measured by periodic sampling and sieving of the raw materials. However, this method takes time in analysis. Patent Literature 1 discloses a technique in which a raw material is automatically sampled to increase the frequency of analysis. If the sampling is performed too often, however, the operation process may be delayed. Also, the sampling, which is for the purpose of inspection, has a problem of representativeness.

Unlike the aforementioned conventional technique in which the particle sizes are measured by sampling and sieving of raw materials, there have been proposed techniques in which the particle size of a raw material during conveyance is measured in real time using, for example, a camera.

For example, Patent Literature 2 discloses a technique for detecting the particle size of a bulk raw material conveyed by a conveyer. The technique involves capturing an image of the bulk raw material on the conveyor to generate image data, determining a brightness distribution from the image data, and detecting the particle size of the bulk raw material using the maximum peak height in the brightness distribution.

Patent Literature 3 discloses a technique in which the water content of a material to be charged into a blast furnace is detected from spectroscopic information that is obtained from near-infrared reflected light included in light reflected from the material to be charged. In this technique, the fine ratio of the material to be charged is detected in real time on the basis of the relation between the water content of the material to be charged and the fine ratio of fines adhering to the material to be charged.

Patent Literature 4 discloses a technique in which an average brightness in image data obtained by capturing an image of lumps of material is determined as a feature quantity. In this technique, the fine ratio, or the ratio of fines adhering to the surface of the lumps of material, is determined from the feature quantity described above.

CITATION LIST

Patent Literature

PTL 1: Japanese Unexamined Patent Application Publication No. 2005-134301

PTL 2: Japanese Unexamined Patent Application Publication No. 2000-329683

PTL 3: Japanese Unexamined Patent Application Publication No. 2015-124436

PTL 4: International Publication No. 2018/101287

SUMMARY

Technical Problem

The conventional techniques described above have the following problems.

Because of constraints in the resolution of the camera, the technique disclosed in Patent Literature 2 cannot fully ensure accuracy in measuring a bulk raw material including adhering fines therearound.

The technique disclosed in Patent Literature 3 cannot ensure a sufficient level of measurement accuracy, because the correlation between the water content of the material to be charged and the fine ratio in the material to be charged is not necessarily high.

Like the technique disclosed in Patent Literature 3, the technique described in Patent Literature 4 cannot ensure a sufficient level of measurement accuracy, because the correlation between the brightness of the camera image and the fine ratio is not necessarily high.

Accordingly, an object of the disclosed embodiments is to solve the problems in the conventional techniques described above. The disclosed embodiments provide a fine ratio measuring method and a fine ratio measuring apparatus that are capable of measuring the fine ratio, or the ratio of fines adhering to the surface of lumps of material, in real time with high accuracy.

Solution to Problem

The inventors have conducted various studies to develop a fine ratio measuring technique that can solve the problems described above. The inventors have found that the fine ratio, or the ratio of fines adhering to the surface of lumps of material, can be measured in real time with high accuracy by the following technique. The technique involves measuring the distance to the lumps of material (fine ratio measurement object) with a rangefinder, determining from the resulting distance data a feature quantity correlated to the fine ratio, and converting the feature quantity to the fine ratio.

The disclosed embodiments, which have been made on the basis of the findings described above, are summarized as follows.

[1] A fine ratio measuring method includes a step (S1) of measuring a distance between a distance measuring device and lumps of material (x), a step (S2) of calculating a feature quantity from distance data obtained in the step (S1), and a step (S3) of converting the feature quantity calculated in the step (S2) to a fine ratio.

[2] In the fine ratio measuring method according to [1], the feature quantity calculated in the step (S2) represents distance variation calculated from the distance data obtained in the step (S1).

[3] In the fine ratio measuring method according to [2], the feature quantity calculated in the step (S2) is based on standard deviations in a standard deviation matrix obtained by applying a standard deviation filter to the distance data obtained in the step (S1).

[4] In the fine ratio measuring method according to [3], the feature quantity calculated in the step (S2) is a modal standard deviation in the standard deviation matrix obtained by applying the standard deviation filter to the distance data obtained in the step (S1).

[5] In the fine ratio measuring method according to [3] or [4], a filtering range of the standard deviation filter is 10×10 pixels or less.

[6] In the fine ratio measuring method according to any one of [1] to [5], in the step (S1), the distance measuring device installed above the lumps of material (x) measures the distance to the lumps of material (x).

[7] A fine ratio measuring apparatus includes a distance measuring device (1) configured to measure a distance to lumps of material (x), and a computing device (2) including a calculating means (2a) and a converting means (2b). The calculating means (2a) is configured to calculate a feature quantity from distance data obtained by the distance measuring device (1), and the converting means (2b) is configured to convert the feature quantity calculated by the calculating means (2a) to a fine ratio.

[8] In the fine ratio measuring apparatus according to [7], the calculating means (2a) calculates the feature quantity representing distance variation from the distance data obtained by the distance measuring device (1).

[9] In the fine ratio measuring apparatus according to [8], the calculating means (2a) applies a standard deviation filter to the distance data obtained by the distance measuring device (1), and calculates the feature quantity on the basis of standard deviations in a resulting standard deviation matrix.

[10] In the fine ratio measuring apparatus according to [9], the calculating means (2a) applies the standard deviation filter to the distance data obtained by the distance measuring device (1), and calculates a modal standard deviation in the resulting standard deviation matrix as the feature quantity.

[11] In the fine ratio measuring apparatus according to [9] or [10], a filtering range of the standard deviation filter is 10×10 pixels or less.

[12] In the fine ratio measuring apparatus according to any one of [7] to [11], the distance measuring device (1) is installed above the lumps of material (x) and measures the distance to the lumps of material (x).

Advantageous Effects

With the disclosed embodiments, the fine ratio, or the ratio of fines adhering to the surface of lumps of material, can be measured in real time with high accuracy. It is thus possible, for example, to accurately know the fine ratio in blast furnace coke (i.e., the ratio of coke fines) before the coke is charged into the blast furnace. This contributes to stable operation of the blast furnace.

DETAILED DESCRIPTION

A fine ratio measuring method according to the disclosed embodiments is a method for measuring a fine ratio in lumps of material (x), on the basis of the amount of fines adhering to the surface of the lumps of material (x). The fine ratio measuring method includes a step (S1) of measuring a distance to the lumps of material (x) with a distance measuring device, a step (S2) of calculating a feature quantity from distance data obtained in the step (S1), and a step (S3) of converting the feature quantity calculated in the step (S2) to a fine ratio.

A fine ratio measuring apparatus according to the disclosed embodiments is used to implement the fine ratio measuring method described above. The fine ratio measuring apparatus includes a distance measuring device 1 configured to measure a distance to the lumps of material (x), and a computing device 2 including a calculating means 2a and a converting means 2b. The calculating means 2a calculates a feature quantity from distance data based on the distance obtained by the distance measuring device 1. The converting means 2b converts the feature quantity calculated by the calculating means 2a to a fine ratio.

Examples of the lumps of material (x) for which the fine ratio is to be measured in the disclosed embodiments include, but are not limited to, lumps of raw materials (e.g., ore and coke) used in metal smelting processes, such as ironmaking processes.

Here, the fine ratio is defined as the ratio of the mass of fines with a predetermined size or less to the total mass of the lumps of material (x) having fines adhering to the surface thereof.

An embodiment will now be described using an example where the lumps of material (x) (fine ratio measurement object) are lumps of coke before being charged into a blast furnace.

Figure 1:
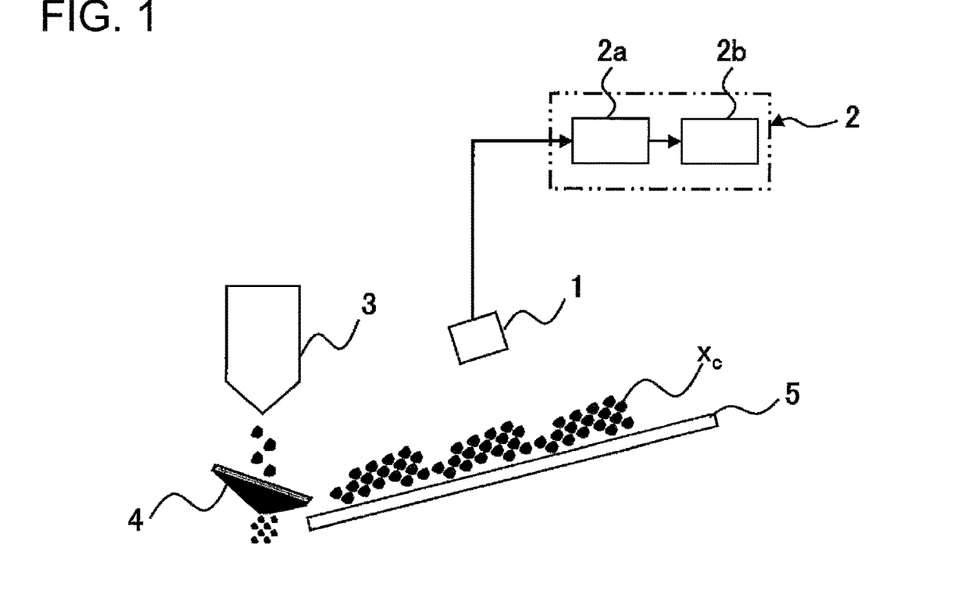
FIG. 1 is an explanatory diagram illustrating an embodiment applied to measurement of the fine ratio in coke before being charged into a blast furnace.

FIG. 1 illustrates an embodiment, and specifically an example where the embodiment is applied to measurement of the fine ratio in coke that is before being charged into the blast furnace. In the drawing, reference sign 3 denotes a hopper, reference sign 4 denotes a sieve, reference sign 5 denotes a conveyer, and reference sign $x_c$ denotes coke which is a fine ratio measurement object. Also, reference signs 1 and 2 denote a distance measuring device and a computing device, respectively, which constitute the fine ratio measuring apparatus according to the disclosed embodiments. The computing device 2 includes the calculating means 2a that calculates a feature quantity from distance data obtained by the distance measuring device 1, and the converting means 2b that converts the feature quantity calculated by the calculating means 2a to a fine ratio.

The coke $x_c$ charged into the blast furnace is stored in the hopper 3. The coke $x_c$ dispensed from the hopper 3 is sieved using the sieve 4 to remove fine powder, transferred onto the conveyer 5, and conveyed by the conveyer 5 to the blast furnace (or a hopper at the top of the furnace). The coke $x_c$ conveyed by the conveyer 5 includes coke particles (lumps) on the sieve 4 and adhering fines (coke fines) adhering to the coke particles without being sieved through the sieve 4.

In this embodiment, the coke $x_c$ conveyed by the conveyer 5 is measured in the following manner to determine the fine ratio, or the ratio of fines mainly constituted by the adhering fines described above.

First, the distance measuring device 1 installed above the conveyer 5 measures the distance to the coke $x_c$ on the conveyer 5, and acquires three-dimensional shape data of the coke $x_c$ (step S1). For example, a two-dimensional laser rangefinder may be used as the distance measuring device 1.

When the laser rangefinder described above is used, the distance to the coke $x_c$ is measured line-by-line by irradiating the coke $x_c$ with laser light in the conveyer width direction. Each line corresponds to the width of the laser light with which the coke $x_c$ is irradiated in the conveyer width direction. Since the coke $x_c$ is being conveyed and moved by the conveyer 5, the three-dimensional shape data of the coke $x_c$ is obtained by linearly measuring the distance to the coke $x_c$ with the laser rangefinder at regular measurement cycles, and then sequentially combining the measured values for the lines. The technique described above is one in which the three-dimensional shape of an object to be measured is acquired by a so-called light-section method. A conventional laser rangefinder and conventional data processing means may be used to perform the technique.

The laser rangefinder is preferably one that has a measurement field as wide as the conveyer width and is capable of measuring the entirety (or entire surface) of the coke $x_c$ conveyed by the conveyer 5. Shorter measurement cycles, particularly 1 kHz or more, are preferable. In this embodiment, the measurement cycles are set to 4 kHz.

The distance measuring device 1 does not necessarily need to be a two-dimensional laser rangefinder. For example, a distance measuring device based on a stereoscopic technique using two cameras may be used.

Figure 2:
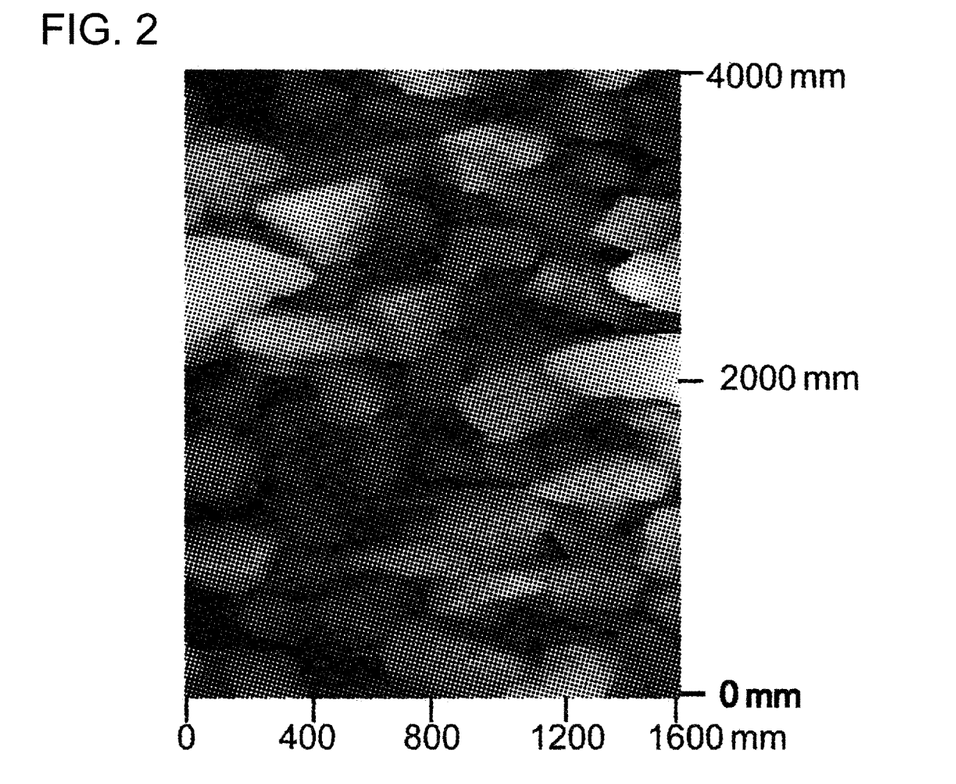
FIG. 2 shows an exemplary image of the three-dimensional shape of coke based on the distance obtained by a distance measuring device in the embodiment illustrated in FIG. 1.

FIG. 2 shows an exemplary image of the three-dimensional shape of the coke $x_c$ (i.e., image of the coke $x_c$ on the conveyer 5 viewed from above), based on the distance obtained by the two-dimensional laser rangefinder. In the grayscale image shown in FIG. 2, whiter areas are higher in height and closer in distance to the rangefinder. The image is 800 pixels wide (in the conveyer width direction) and 1000 pixels long (in the conveyor moving direction). Each pixel of the image is 2 mm wide and 4 mm long. The distance is determined for each pixel.

That is, the image shown in FIG. 2 is obtained by combining 1000 lines of data of distance (hereinafter also referred to as "distance data") in the conveyer width direction, with each line containing 800 pixels. The distance data of 800 pixels×1000 pixels is thus obtained. The resolution in the height direction is 5 µm.

In a conventional image processing technique performed on three-dimensional shape data, the three-dimensional shape data of the coke including irregularities is typically subjected to signal processing, by which the coke is separated into individual particles. The number of the coke particles obtained by the particle separation processing is counted for each size range to create a histogram and calculate a particle size distribution.

For example, when the distance measuring device 1 has a minimum resolution of 4 mm×2 mm in the length and width direction and a resolution of 5 µm in the height direction, since coke charged into the blast furnace typically has a particle size of 35 mm or more, the resolutions are sufficient to measure the particle size of coke particles (lumps) through the signal processing. However, adhering fines (coke fines) adhering to the surface of coke particles (lumps) often include those having a particle size of 1 mm or less. If such adhering fines are spherical, the resolution of the distance measuring device 1 is insufficient in the length and width direction, although it is high enough in the height direction. Accordingly, unlike in the case of coke particles (lumps), it is difficult to count the number of adhering fines and determine the fine ratio.

If the distance measuring device is brought as close as possible to the coke to narrow the width of the measurement range of the distance measuring device and increase the resolution in the length and width direction, it is possible to capture the adhering fines on the coke surface and measure the fine ratio. However, when the distance measuring device is brought close to the coke, adhering fines on only part of the coke can be captured. It is therefore not possible to determine the fine ratio for the entire coke conveyed by the conveyer (i.e., fine ratio across the conveyer width). Installing many distance measuring devices may be possible. However, this makes data processing complex, adds constraints to installation, and is costly.

In the disclosed embodiments, where the entire conveyer width is contained within the measurement field, the fine ratio can be measured with high accuracy even when the resolution in the length and width direction is not high enough. That is, the disclosed embodiments are designed to measure the distance to the coke $x_c$, determine from the resulting distance data a feature quantity representing microscopic distance variation, and convert the feature quantity to a fine ratio, so that the fine ratio, or the ratio of fines adhering to the surface of the coke $x_c$, is determined.

In the disclosed embodiments, a feature quantity representing microscopic distance variation is calculated from distance data (three-dimensional shape data of coke) measured by the distance measuring device 1 as described above (step S2). The resolution of the distance data obtained by the distance measuring device 1 is not high enough in the length and width direction to measure the fine ratio, but is high enough in the height direction even when the entire conveyer width is contained within the measurement field.

The inventors have found that as the amount of fines adhering to the coke surface increases (i.e., as the fine ratio increases), microscopic irregularities in the coke surface in the height direction within the three-dimensional shape increase (i.e., microscopic distance variation of coke in the height direction increases). Accordingly, the disclosed embodiments use the microscopic distance variation as the feature quantity and determines the fine ratio from the feature quantity.

This embodiment considers the microscopic distance variation as local height variation in a given place, applies a standard deviation filter (i.e., filter for calculating standard deviations) having a small filtering range to distance data, and derives a feature quantity from the resulting standard deviations. The larger the microscopic irregularities in the coke surface resulting from a high fine ratio, the greater the standard deviations obtained by applying the standard deviation filter. The feature quantity is thus derived from the standard deviations.

First, the acquired distance data is divided into pixels. For example, the distance data shown in FIG. 2 is divided into 800×1000 pixels. Next, an 800×1000 matrix is created by assigning a corresponding distance to each pixel. Then, a commonly used, standard deviation filter having a filtering range of a 3×3 matrix (corresponding to 3×3 pixels) is applied to the distance data of the 800×1000 matrix to determine a standard deviation for each 3×3 matrix. The feature quantity is derived from the resulting standard deviations.

Figure 3:
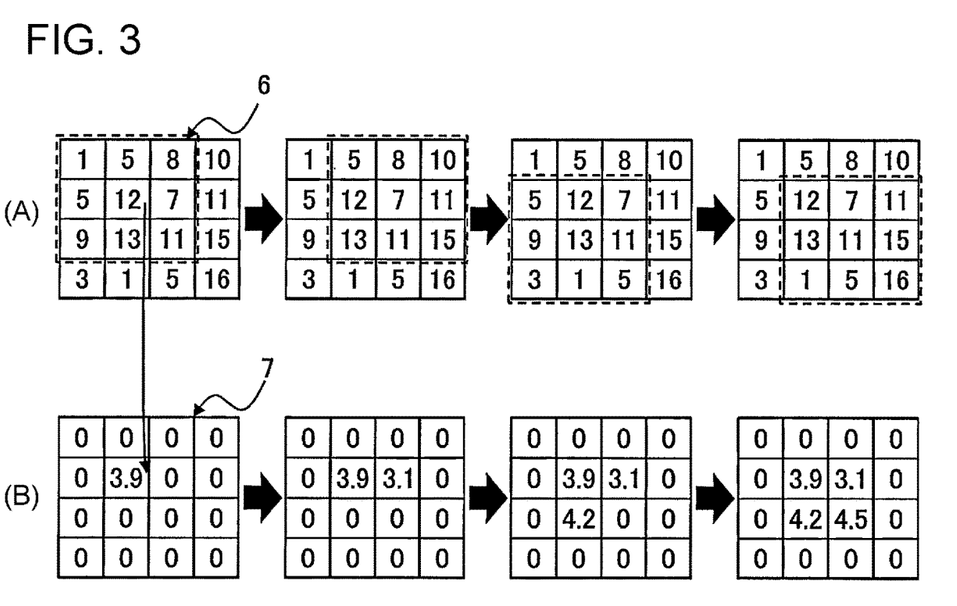
FIG. 3 is an explanatory diagram illustrating an exemplary calculation technique that is used when, in calculating a feature quantity from distance data obtained by the distance measuring device, a standard deviation filter is applied to the distance data to determine a standard deviation matrix of the distance data, according to an embodiment.

FIG. 3 illustrates an exemplary calculation technique (image of calculation) which involves applying the standard deviation filter to distance data. In FIG. 3, reference sign 6 denotes a standard deviation filter, and reference sign 7 denotes a 4×4 standard deviation matrix for output. In this example, the standard deviation filter 6 with a filtering range of a 3×3 matrix is applied to distance data of a 4×4 matrix (corresponding to 4×4 pixels). FIG. 3(A) shows an image of applying the standard deviation filter 6 with a 3×3 matrix to a 4×4 input matrix. FIG. 3(B) shows an image of storing calculated values in the 4×4 standard deviation matrix for output. The standard deviation matrix for output illustrated in FIG. 3(B) is generated from the input matrix illustrated in FIG. 3(A). Note that numbers in FIG. 3(A) and FIG. 3(B) are examples presented for the purpose of explanation.

A detailed procedure will now be described.

First, the 4×4 output matrix 7 is generated and 0s (zeros) are stored throughout the output matrix 7. As illustrated in FIG. 3(A), the standard deviation of a total of 9 pixels within a target filtering range is calculated and the calculated standard deviation is output at a position in the output matrix 7 corresponding to the center position in the filtering range. The standard deviation filter 6 is then shifted to the next range, where the same process is repeated. In the example of FIG. 3, the filtering calculation described above is performed a total of four times for one 4×4 input matrix.

In the case of the distance data shown in FIG. 2, this calculation is applied to the distance data of the 800×1000 matrix, so that a standard deviation matrix for the distance data of the 800×1000 matrix is output. The feature quantity is determined using the 800×1000 standard deviation matrix.

To capture microscopic variation, the standard deviation filter 6 preferably has a smaller filtering range (number of pixels). The filtering range is preferably 10×10 pixels or less (or a total of 100 pixels or less), and more preferably 5×5 pixels or less (or a total of 25 pixels or less). The filtering range is particularly preferably 3×3 pixels (or a total of 9 pixels) described above, and most preferably 2×2 pixels. This is because with a small filtering range, it is possible to reduce the influence of, for example, the shape of coke or the inclination of the measurement surface of coke with respect to the distance measuring device.

Figure 4:
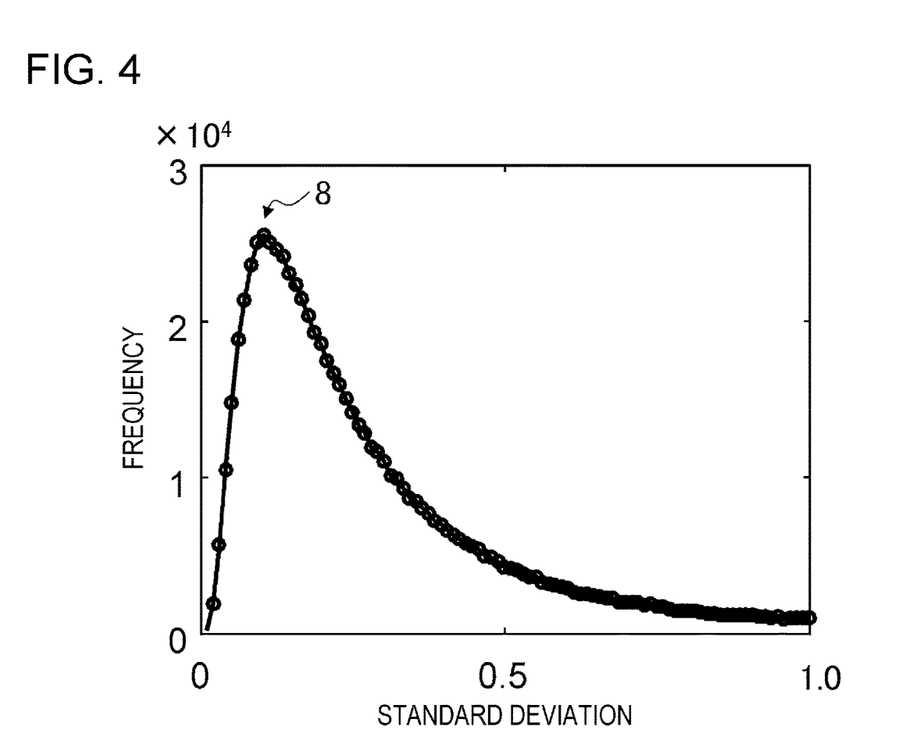
FIG. 4 is a graph showing the distribution of standard deviations in the standard deviation matrix determined by the calculation illustrated in FIG. 3.

FIG. 4 is a graph showing the distribution of standard deviations in the standard deviation matrix obtained by applying the procedure described above to the distance data shown in FIG. 2. A peak standard deviation indicated by reference sign 8 in the drawing represents a modal standard deviation. In this example, the standard deviations in the standard deviation matrix are divided into a sufficient number of classes (50000 classes in this example (with intervals of 0.00002)), and the most frequent standard deviation in the classes is defined as the modal standard deviation. Note that this excludes the frequency of a standard deviation of 0 (zero).

Figure 5:
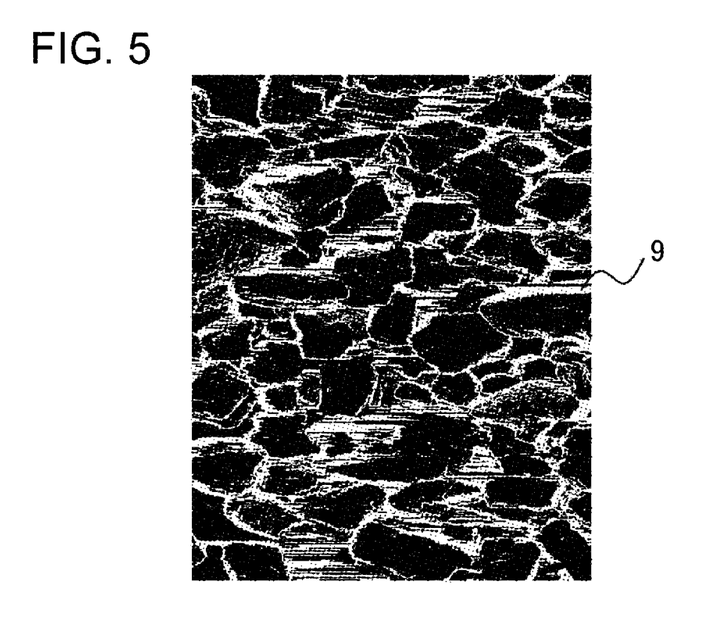
FIG. 5 shows a white and black binary image produced with a threshold of 0.5, which is a standard deviation in an 800×1000 standard deviation matrix output when a standard deviation filter with a filtering range of a 3×3 matrix (3×3 pixels) is applied to the distance data of the image shown in FIG. 2.

FIG. 5 shows a white and black binary image produced with a threshold of 0.5, which is a standard deviation in the 800×1000 standard deviation matrix output by applying the standard deviation filter with a filtering range of a 3×3 matrix (3×3 pixels) to the distance data in FIG. 2. The white portion of the binary image corresponds to a standard deviation of 0.5 or more, and the black portion of the binary image corresponds to a standard deviation of less than 0.5. The comparison between FIG. 5 and FIG. 2 reveals that many matrix elements having a standard deviation of 0.5 or more are located at steps or boundaries between overlapping pieces of coke (reference sign 9 in FIG. 5).

Figure 6:
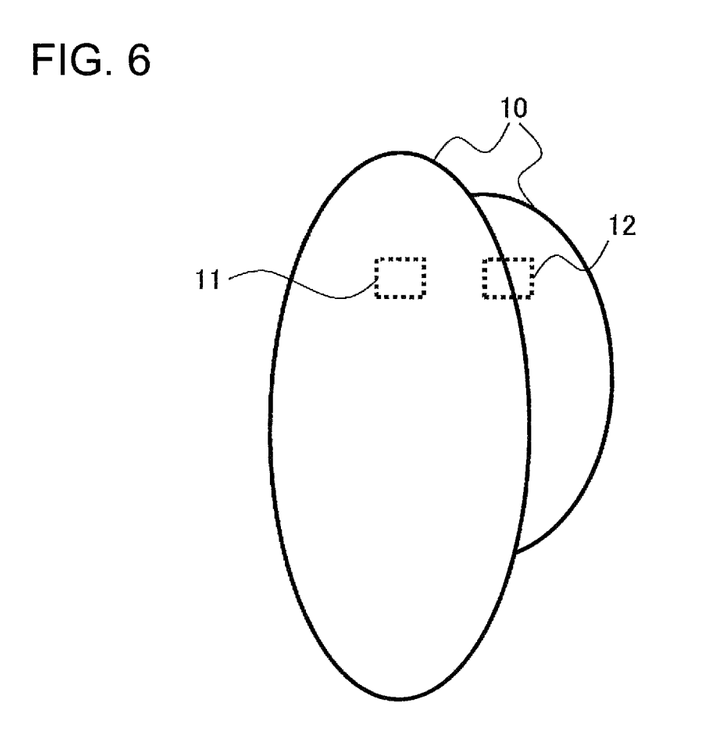
FIG. 6 is a schematic diagram illustrating an image of overlapping coke particles (lumps).

FIG. 6 is a schematic diagram illustrating an image of overlapping coke particles (lumps). In the drawing, reference sign 10 denotes overlapping pieces of coke. Reference sign 11 denotes the standard deviation filter applied to a coke surface, and reference sign 12 denotes the standard deviation filter applied to a step or boundary between the overlapping pieces of coke. As described above, in the standard deviation matrix obtained from the distance data, there are many values calculated by applying the standard deviation filter to steps or boundaries between overlapping pieces of coke, and the standard deviations are very large.

In the disclosed embodiments, standard deviations representing microscopic variation caused by the presence of adhering fines adhering to the coke surface should be included in the feature quantity. Accordingly, it is preferable to exclude standard deviations affected by the presence of steps or boundaries between overlapping pieces of coke. An average standard deviation in the standard deviation matrix (e.g., 800×1000 standard deviation matrix) includes disturbances caused by the presence of steps or boundaries between overlapping pieces of coke. On the other hand, the modal standard deviation 8 in the standard deviation matrix shown in FIG. 4 is affected very little by the presence of steps or boundaries between overlapping pieces of coke if coke particles (lumps) are large enough. That is, although the average standard deviation in the standard deviation matrix may be used as the feature quantity, it is preferable that the modal standard deviation 8 in the standard deviation matrix shown in FIG. 4 be used as the feature quantity.

In the disclosed embodiments, a method using a standard deviation filter is applied to calculation of the feature quantity representing microscopic distance variation. However, the method is not limited to this. For example, a method using high-frequency components of a two-dimensional Fourier transform may be applied by considering the 800×1000 matrix as an image.

Next, the feature quantity obtained as described above is converted to a fine ratio (step S3). This conversion is made using a coefficient (relational expression) determined in advance on the basis of the correlation between the feature quantity and the known fine ratio.

Figure 7:
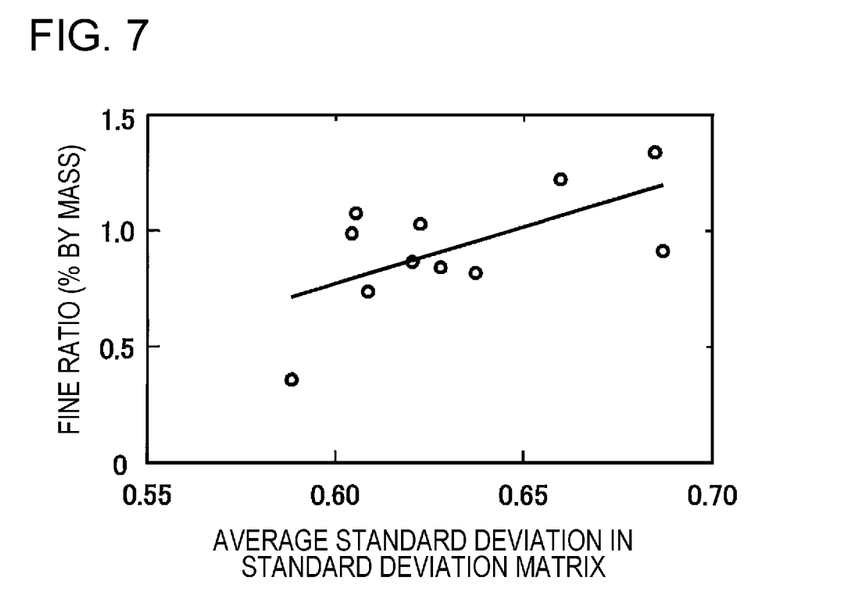
FIG. 7 is a graph showing a correlation between the feature quantity determined in an embodiment and the known fine ratio, where an average standard deviation in the standard deviation matrix is used as the feature quantity.
Figure 8:
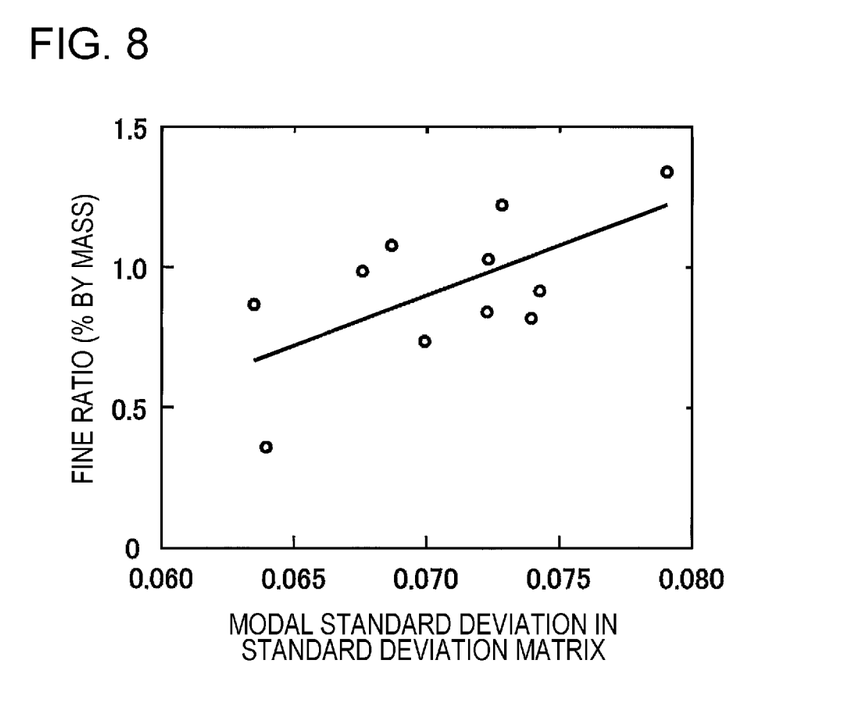
FIG. 8 is a graph showing a correlation between the feature quantity determined in an embodiment and the known fine ratio, where a modal standard deviation in the standard deviation matrix is used as the feature quantity.

FIG. 7 and FIG. 8 each show a correlation between the feature quantity and the known fine ratio. An average standard deviation in the standard deviation matrix is used as the feature quantity in FIG. 7, and a modal standard deviation in the standard deviation matrix is used as the feature quantity in FIG. 8. FIG. 7 and FIG. 8 show results obtained by using lumps of coke as the lumps of material described above. The lumps of coke are of a particle size of 35 mm or more, and have coke fines with a particle size of 1 mm or less adhering to the surface thereof. In FIG. 7 and FIG. 8, the vertical axis represents the fine ratio (% by mass) of the coke fines of 1 mm or less adhering to the lumps of coke, and the horizontal axis represents the feature quantity representing microscopic variation calculated from distance data obtained by measuring the lumps of coke having coke fines of 1 mm or less adhering thereto.

The lumps of coke with a particle size of 35 mm or more, used in testing, were prepared by sieving the coke using a sieve with a mesh size of 35 mm. A hundred or more lumps of coke were used. The fine ratio of the coke fines of 1 mm or less, adhering to the surface of the lumps of coke, was calculated as follows. First, the lumps of coke were dried at 120° C. to 200° C. for 4 hours or more to a constant weight, and then sieved using a sieve with a mesh size of 1 mm. The fine ratio, described above, was calculated as the ratio (or percentage) of the difference in the mass of the lumps of coke before and after sieving to the mass before sieving. This method uses the fact that adhering fines fall off when dry.

FIG. 7 and FIG. 8 both show a clear correlation between the feature quantity and the fine ratio. In the case of the average standard deviation in the standard deviation matrix shown in FIG. 7, however, the correlation coefficient is R=0.60 and the measurement error (root mean square error) $\sigma$ is $\sigma$=0.23, whereas in the case of the modal standard deviation in the standard deviation matrix shown in FIG. 8, the correlation coefficient is R=0.70 and the measurement error is $\sigma$=0.20. The modal standard deviation in the standard deviation matrix thus shows a better correlation. Therefore, when there are many steps and boundaries between overlapping pieces of coke, it is desirable to use the modal standard deviation in the standard deviation matrix. A slope "a" and a y-intercept "b" obtained by linear regression of the feature quantity and the known fine ratio are a=4.89 and b=−2.16 in FIG. 7, and a=35.6 and b=−1.6 in FIG. 8. Although linear regression is performed here, multiple linear regression or non-linear regression may be performed.

In the disclosed embodiments, a coefficient (relational expression) is determined in advance on the basis of the correlation between the feature quantity (preferably, the modal standard deviation in the standard deviation matrix) and the known fine ratio, such as those shown in FIG. 7 and FIG. 8. Then, the feature quantity (preferably, the modal standard deviation in the standard deviation matrix) is converted to the fine ratio using the coefficient. The fine ratio in the coke is thus measured with high measurement accuracy (e.g., with a measurement error $\sigma$ of 0.3 or less).

Figure 9:
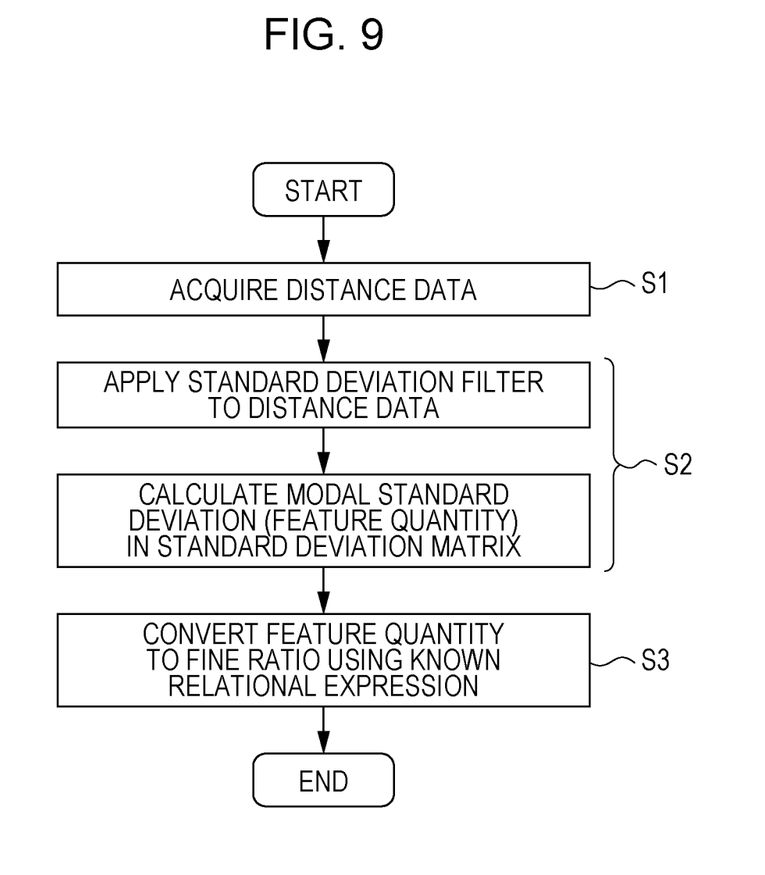
FIG. 9 is a flowchart of an embodiment.

FIG. 9 is a flowchart of the embodiment described above. In this embodiment, as described above, a coefficient (relational expression) for converting the feature quantity to the fine ratio is determined in advance from the correlation between the feature quantity and the known fine ratio.

The distance measuring device 1 measures the distance to the lumps of material (x) (fine ratio measurement object), such as the coke $x_c$ conveyed by the conveyor, to acquire distance data (three-dimensional shape data) (step S1). Next, the calculating means 2a of the computing device 2 applies the standard deviation filter to the distance data to determine standard deviations, calculates a modal standard deviation in the standard deviation matrix, and uses the modal standard deviation as the feature quantity (step S2). Next, the converting means 2b of the computing device 2 converts the feature quantity to a fine ratio using the known coefficient (relational expression) to determine the fine ratio, or the ratio of fines adhering to the lumps of material x (step S3).

Then, step S1 is performed at predetermined measurement cycles. Each time the distance data is obtained in step S1, step S2 and step S3 are performed to determine the fine ratio.

The fine ratio in the lumps of material (x) is thus measured in real time with high accuracy.

The embodiment applies the disclosed embodiments to the measurement of the fine ratio in the coke $x_c$ before being charged into the blast furnace. The disclosed embodiments are applicable not only to this, but also to measurement of the fine ratio in the lumps of material (x) of various kinds.

The disclosed embodiments are a method that is suitable for measuring, in real time, the fine ratio in the lumps of material (x) (e.g., coke or ore) being conveyed, for example, by a conveyer. The disclosed embodiments are also applicable to measurement of the fine ratio in the lumps of material (x) at rest. This is achieved by moving the distance measuring device 1 to measure the three-dimensional shape of the lumps of material (x) at rest.

Although the adhering fines have been described as being 1 mm or less in size, the size is not limited to this and may be appropriately determined. For example, even when the adhering fines are 2 mm or less (not 1 mm or less) in size, the fine ratio can be measured by determining the correlation between the feature quantity and the fine ratio in advance.

The invention claimed is:

1. A fine ratio measuring method comprising:
   a step (S1) of measuring a distance between a laser rangefinder and lumps of material conveyed on a conveyer, wherein in step (S1), the laser rangefinder is installed above the lumps of material such that an entire width of the conveyer is contained within a measurement field of the laser rangefinder that measures the distance to the lumps of material;
   a step (S2) of calculating a feature quantity from the measured distance obtained in step (S1); and
   a step (S3) of converting the feature quantity calculated in step (S2) to a fine ratio, wherein the fine ratio is defined as a ratio of mass of fine particles with a predetermined size or less to a total mass of the lumps of material, wherein
   the feature quantity calculated in step (S2) represents distance variation calculated from the measured distance obtained in step (S1),
   the feature quantity calculated in step (S2) is based on standard deviations in a standard deviation matrix obtained by applying a standard deviation filter to the measured distance obtained in step (S1), and
   the feature quantity calculated in step (S2) is a modal standard deviation in the standard deviation matrix obtained by applying the standard deviation filter to the measured distance obtained in step (S1).

2. The fine ratio measuring method according to claim 1, wherein a filtering range of the standard deviation filter is 10×10 pixels or less.

3. A fine ratio measuring apparatus comprising:
   a laser rangefinder configured to measure a distance to lumps of material conveyed on a conveyer, wherein the laser rangefinder is installed above the lumps of material such that an entire width of the conveyer is contained within a measurement field of the laser rangefinder that measures the distance to the lumps of material; and
   a computing device configured to calculate a feature quantity from the measured distance obtained by the laser rangefinder, and convert the calculated feature quantity to a fine ratio, wherein the fine ratio is defined as a ratio of mass of fine particles with a predetermined size or less to a total mass of the lumps of material, wherein the computing device calculates the feature quantity representing distance variation from the measured distance obtained by the laser rangefinder, the computing device applies a standard deviation filter to the measured distance obtained by the laser rangefinder, and calculates the feature quantity on the basis of standard deviations in a resulting standard deviation matrix, and the computing device applies the standard deviation filter to the measured distance obtained by the laser rangefinder, and calculates a modal standard deviation in the resulting standard deviation matrix as the feature quantity.

4. The fine ratio measuring apparatus according to claim 3, wherein a filtering range of the standard deviation filter is 10×10 pixels or less.

* * * * *